United States Patent [19]

Kang et al.

[11] Patent Number: 5,656,827

[45] Date of Patent: Aug. 12, 1997

[54] CHEMICAL SENSOR UTILIZING A CHEMICALLY SENSITIVE ELECTRODE IN COMBINATION WITH THIN DIAMOND LAYERS

[75] Inventors: Weng Poo Kang, Nashville; Jimmy Lee Davidson, Brentwood; David V. Kerns, Jr., Nashville, all of Tenn.

[73] Assignee: Vanderbilt University, Nashville, Tenn.

[21] Appl. No.: 453,954

[22] Filed: May 30, 1995

[51] Int. Cl.$^6$ .................................................. H01L 31/0312
[52] U.S. Cl. .................. 257/76; 257/77; 257/252; 257/253; 257/414; 204/419; 204/426; 204/431
[58] Field of Search .................................. 257/252, 253, 257/414, 76, 77; 204/431, 424, 426, 419, 416

[56] References Cited

U.S. PATENT DOCUMENTS 5,216,249  6/1993  Jones et al. ................... 250/370.05 X
5,285,084  2/1994  Von Windheim ........................ 257/77
5,362,975  11/1994 Von Windheim ........................ 257/76
5,493,131  2/1996  Miyata et al. ...................... 257/76 X

FOREIGN PATENT DOCUMENTS 4258756  9/1992  Japan .
5018935  1/1993  Japan .

*Primary Examiner*—William Mintel
*Attorney, Agent, or Firm*—Waddey & Patterson; Mark J. Patterson

[57] ABSTRACT

A solid state chemical sensing device is described in which a chemically sensitive electrode, and at least one diamond film are deposited on a conductive or insulating substrate. The device forms a sensing structure in which conduction of current through the device in the presence of a target chemical is dominated by space charged limited current, thereby providing enhanced sensitivity and selectivity.

35 Claims, 8 Drawing Sheets

CHEMICAL SENSOR UTILIZING A CHEMICALLY SENSITIVE ELECTRODE IN COMBINATION WITH THIN DIAMOND LAYERS

BACKGROUND OF THE INVENTION

The present invention relates to solid state devices for sensing the presence and mount of a gas or other targeted chemical. More particularly, this invention relates to solid state chemical sensing devices fabricated using a thin-layered diamond structure combined with one or more chemical sensitive electrodes to enhance selective detection of specific chemicals including gas concentrations of certain chemical species, concentrations of ions in liquids, and concentration of enzymes for biochemical sensing.

The first active microelectronic-based gas-sensing device was reported by Lundstrom in 1975. I Lundstrom, S. Shivaraman, C. Svensson and L. Lundkvist, "A hydrogen-sensitive MOS field-effect transistor," *Appl. Phys. Lett.*, 26, pp. 55–57, 1975. Since then, extensive research efforts have been directed toward the development of catalytic-gate microelectronic gas sensors based on Schottky diodes, MOS capacitors, and MISFETs using silicon technology. The majority of these prior art devices have been fabricated using silicon as a semiconducting layer with catalytic metals such as palladium, platinum or other noble metal as the gate electrode for detection of hydrogen and hydrogen-containing gases. Sensitivity has been reported for hydrogen [I Lundstrom, S. Shivaraman, C. Svensson and L. Lundkvist, "A hydrogen-sensitive MOS field-effect transistor," *Appl. Phys. Lett.*, 26, pp. 55–57, 1975; I. Lundstrom, "Hydrogen sensitive MOS-structures," *Sensors and Actuators*, vol. 1, pp. 400–426, 1981; T. Poteat and B. Lalevic, "Transition metal gate MOS gaseous detectors," *IEEE Trans. Electron Devices*, vol. ED-29, pp. 123–129, 1982; P. Ruthes, S. Ashor, S. Fonash and J. Ruths, "A study of Pd-MIS Schottky barrier diode detector," *IEEE Trans. Electron Devices*, vol. ED-28, pp. 1003–1009, 1981], hydrocarbons [T. Poteat and B. Lalevic, "Transition metal gate MOS gaseous detectors," *IEEE Trans. Electron Devices*, vol. ED-29, pp. 123–129, 1982; P. Ruthes, S. Ashor, S. Fonash and J. Ruths, "A study of Pd-MIS Schottky barrier diode detector," *IEEE Trans. Electron Devices*, vol. ED-28, pp. 1003–1009, 1981; U. Ackelid, F. Winquist and I. Lundstrom, "MOS structures with thermally activated sensitivity to ethanol vapor and unsaturated hydrocarbons," *Proc. 2nd Ins. Meet Chemical Sensors*, 1986, Bordeaux, pp. 395–398], alcohol vapor [U. Ackelid, F. Winquist and I. Lundstrom, "MOS structures with thermally activated sensitivity to ethanol vapor and unsaturated hydrocarbons," *Proc. 2nd Int. Meet Chemical Sensors*, 1986, Bordeaux, pp. 395–398; N. Yamamoto, S. Tonamura, T. Matsuoka and S. Tsubomura, "A study on a palladium titanium oxide Schottky diode as a detector for gaseous components," *Surface Sci.*, 92, pp. 400–406, 1908; U. Ackelid, M. Armgarth, A. Spetz and I. Lundstrom, "Ethanol sensitivity of palladium-gate metal-oxide-semiconductor structures," *IEEE Electron Device Lett.*, EDL-7, pp. 353–355, 1985]; hydrogen sulphide [M. S. Shivaraman, "Detection of $H_2S$ with Pd gate MOSFETs," *J. Appl. Phys.*, 47, pp. 3592–3593, 1976; J. P. Couput, B. Cornut, C. Chambu and S. Chouvet, "A reversible hydrogen sulphide sensitive Pd-gate MOS transistor," *Proc. Int. Meet. Chemical Sensors*, 1983, Fakuoka, pp. 468–472], and ammonia [I. Lundstrom, M. Armgarth, A. Spetz, and F. Winquist, "Physics of ammonia sensitive metal oxide semiconductor structures," *Proc. 2nd Int. Meet. Chemical Sensors*, 1986, Bordeaux, pp. 387–390; J. F. Ross, I. Robins and B. C. Webb, "The ammonia sensitivity of Platinum gate MOSFET device: dependence on gate electrode morphology," *Sensors and Actuators*, 11, pp. 73–90, 1987].

Research has also been conducted for the detection of other gases through the use of perforated gate structures (K. Dobos, D. Krey and G. Zimmer, "CO-sensitive MOSFET with $SnO_2$-, Pd-, and Pt-gate," *Proc. Int. Meet. Chemical Sensors*, 1983, Fukuoka, pp. 464–467), metal alloys [R. C. Huges, W. K. Schubert, T. E. Zipperian, J. L. Rodriguez and T. A. Plut, *J. Appl. Phys.*, 62, 1074, 1987], or bilayer catalysts [W. P. Kang and C. K. Kim, "Performance analysis of a new MIS capacitor incorporated with $Pt-SnO_x$ catalytic layers for the detection of $O_2$ and CO gases," *J. Appl. Phys.*, 75, pp. 4237–4242, 1994]. The sensitivity and selectivity of gas sensors which use catalytic metal gates depend on parameters such as the composition and microstructure of the metal gate, and the operating temperature of the sensor.

Many interesting applications have been demonstrated and practical devices have been commercialized using microelectronic-based gas sensors. However, the relatively limited temperature operating range (<200° C.) of a silicon-based device has prevented the widespread utilization of these sensors, particularly for the detection of toxic gases from the combustion process and in sire emission control at high temperature. This limitation critically stifles the full exploitation of microelectronic-based devices for chemical sensing applications.

The prior art also has suggested the use of doped and intrinsic polycrystalline diamond in a solid state device which potentially could be used in gas sensing applications. The primary advantages in using polycrystalline diamond thin film structures for chemical sensing applications are wider and/or higher temperature operating range, simplicity in the fabrication process, flexibility in the choice of substrates, and compatibility with silicon microfabrication technology. Moreover, diamond films created using plasma-enhanced chemical vapor deposition (PECVD) possess many desirable material properties, including high thermal conductivity, chemical inertness, electrical stability, and compatibility with hostile environments. Therefore, microelectronic chemical sensors utilizing polycrystalline diamond technology can lead to high temperature capability, high performance, high reliability, low cost, and potentially be extended as a result of smart functionality, such as, diagnostics, self-calibration, fault tolerance and multi-sensor functions.

Recent advances in the PECVD process have resulted in the realization of high quality polycrystalline diamond films for device applications. Microelectronic devices such as Schottky diodes, and field-effect-transistors FET's [A. J. Tessmer, L. S. Plano and D. L. Dreifus, "High temperature operation of polycrystalline diamond FET," *IEEE Electron Device Lea.*, vol. 14, no. 2, pp. 66–68, 1993; G. Sh. Gildenblat, S. A. Grot, C. W. Hatfield, A. R. Badzian and T. Badzian, "High Temperature Schottky diodes with t-film diamond base," *IEEE Electron Device Lett.*, vol. 11, No. 9, pp. 371–372, 1990] have been fabricated for high temperature (T>500° C.) applications. Unfortunately, previous attempts to fabricate and operate a diamond-based chemical sensor have not produced devices having optimal performance characteristics, particularly in chemical sensitivity and selectivity. For example, a diamond-based MIS Schottky diode chemical sensor is described in U.S. Pat. No. 5,285,084, issued Feb. 8, 1994. The '084 sensor is claimed to be barrier dominated. The top metal contact in the '084 device forms a Schottky barrier of a predetermined barrier height prior to gas detection. The change in barrier height upon gas adsorption would lead to a change in I-V characteristics in the sensor, generally described in the literature as:

$$I = AA^{**}T^2 \exp(-\phi_b/\phi_T)[\exp(V/n\phi_T)-1]$$

where k is the Boltzmann constant, T is in degrees Kelvin, $A^{**}$ is the effective Richardson constant, A is the junction area, n is the ideality factor, and $\phi_T = kT/q$. Operation of the '084 device (or any other Schottky barrier chemical sensor) is therefore controlled by the thermionic emission process. Fabrication and operation of a solid state device whereby conduction of current through the sensor is barrier dominated and controlled by thermionic emission results in poor sensitivity and selectivity. The optimal mechanism for detection of a gas or other chemical in a solid state sensing structure is not to determine a shift in a characteristic Schottky barrier curve, as demonstrated by the dashed line curves plotted on FIG. 12. Consequently, a diamond-based Schottky diode structure is not preferred for high performance chemical sensing applications.

What is needed, then, is a solid state chemical sensor which is easy to fabricate, which offers high sensitivity and selectivity, and which can be reliably operated at high temperatures and under other harsh environmental conditions.

SUMMARY OF THE INVENTION

An object of the present invention is to provide a solid state chemical sensor fabricated using CVD diamond film.

Another object of the invention is to provide a diamond-based chemical sensor which offers high sensitivity and selectivity.

A further object of the invention is to fabricate a diamond-based chemical sensor which does not utilize a Schottky barrier for chemical sensing.

Yet another object of the invention is to provide a solid state chemical sensor which can be easily manufactured with an array of multiple sensing structures on a single substrate, including isolated sensing structures for temperature compensation.

To achieve these and other objects of the invention which will become apparent from the drawings and description of the preferred embodiments, the novel chemical sensor of the present invention utilizes polycrystalline diamond technology in conjunction with suitable chemical-sensitive electrode layers to achieve high sensitivity and selectivity for a specific chemical or group of chemicals. The invention includes a novel family of ragged high temperature microelectronic chemical/gas sensors, operable in harsh environments, previously not achievable with conventional technology. Potential applications include in situ emission monitoring and control of toxic or combustible gases, detection of certain chemical species in liquid, and detection of enzymes for biochemical applications. The functionality of the new sensor can be extended by use of a "smart" sensor interface for diagnostics, self-calibration, fault tolerance and multi-sensor functions.

The novel family of diamond-based chemical/gas sensors described herein includes sensors having sensing structures in a discrete configuration or in arrays, for continuous detection and emission control of one or more hazardous chemicals over a wide/high temperature range. Utilizing diamond material provides improved sensitivity, increased dynamic range, and enhanced hostile environment tolerance.

The chemically sensitive electrodes of the invention are fabricated of a catalytic metal, a combination of a catalyst with a solid-electrolyte, a catalyst with a metal-oxide, or a catalyst with an organic material, or other material which is electronically reactive to the presence of certain chemicals. The chemical sensitive electrode combined with one or more thin film diamond layers allows tailoring of chemical sensitivity and selectivity to a specific chemical.

The sensor of this invention can include an integrally fabricated temperature sensor, in the form of a second sensing structure deposited on the device substrate and covered with a passivation layer that isolates the second identical sensing structure from ambient chemicals. This allows for built-in temperature compensation, measurement, and self-calibration. In a further embodiment of the sensor, an integral device heater provides temperature compensation and robust temperature scanning, for enhancing selectivity and reducing chemical interference, as well as a means for eliminating water vapor as a performance factor.

In each embodiment of the invention, the sensor is fabricated so that it will operate, when in the presence of a target chemical, not as a Schottky diode but in a space-charge limited current region, i.e., where conduction of current through the sensor structure is electric field dominated and controlled by space-charge limited current.

DESCRIPTION OF THE PREFERRED EMBODIMENTS

Figure 11:
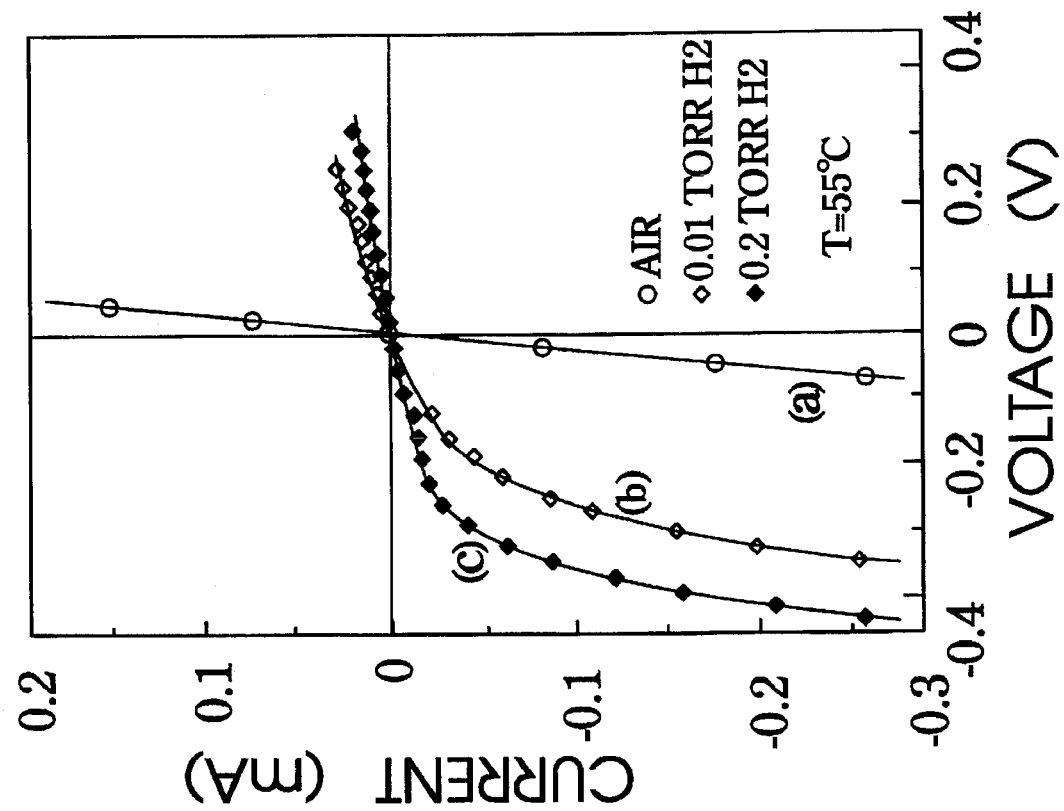
FIG. 11 is a graph showing the relationship between sensor voltage and sensor current using a chemical sensing device of the present invention, when the sensor is exposed to air and to increasing concentrations of hydrogen gas.
Figure 10:
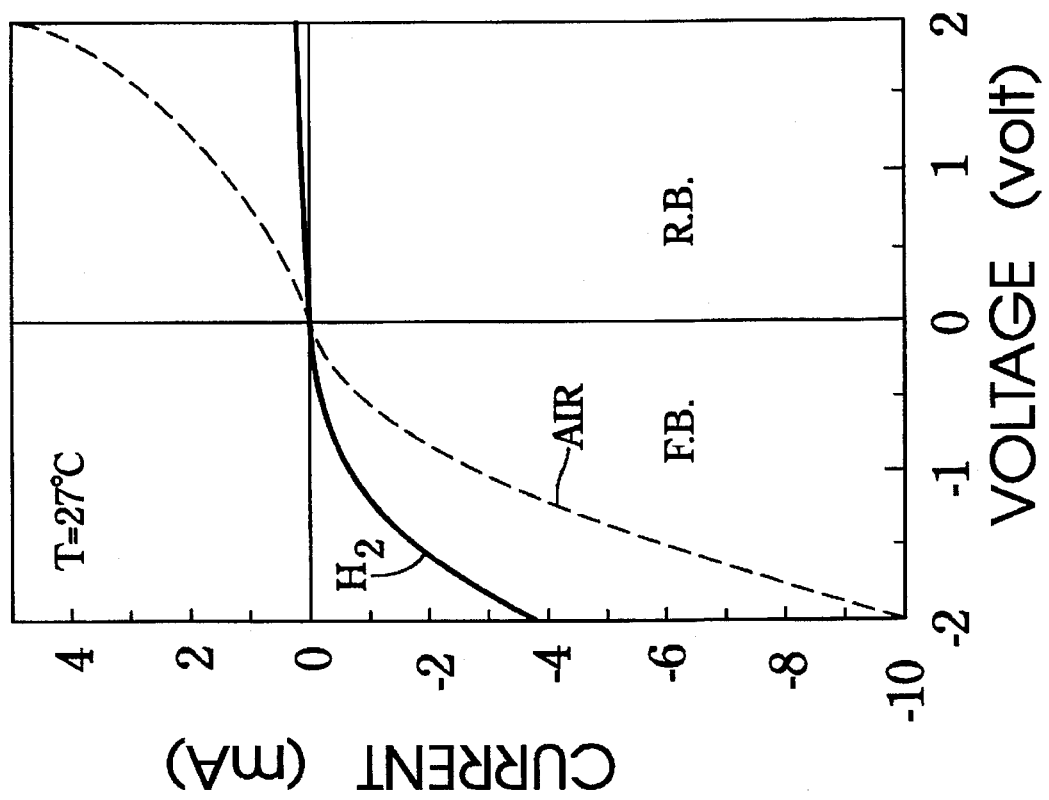
FIG. 10 is a graph showing the relationship between the voltage applied to a chemical sensor of the present invention and corresponding current conducted through the sensor, with the sensor in ambient air and then exposed to hydrogen gas.
Figure 12:
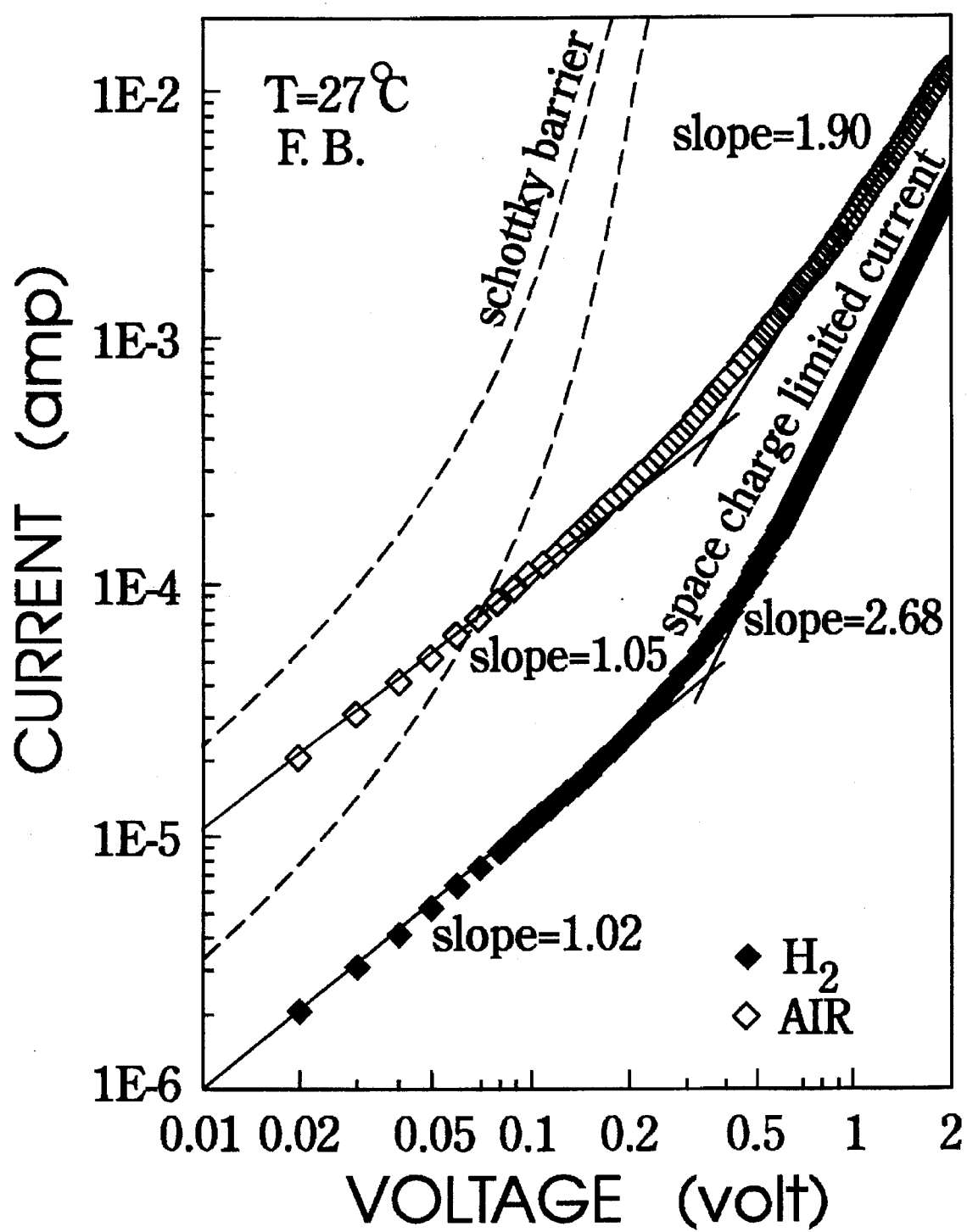
FIG. 12 is a graph of the sensor voltage-current relationship, comparing a prior art diamond Schottky barrier sensor (represented by the dashed lines) and the chemical sensor of the present invention, when operated in the space charged limited current region.

A novel feature of the diamond-based chemical sensor of the present invention is that the chemically-sensitive-electrode/intrinsic diamond/doped-diamond sensing structure is fabricated to operate distinctly different from the "Schottky diode" gas sensors of the prior art. Specifically, a sensing structure is formed whereby current through the sensor is characterized by electric field dominated conduction controlled by space-charge-limited-current (SCLC), as opposed to barrier dominated conduction controlled by thermionic emission. FIGS. 10, 11, and 12 graphically illustrate empirical data describing the voltage-current relationship in the sensing device of the present invention, as compared to prior art Schottky barrier diamond sensing devices shown by the dashed lines on FIG. 12.

To obtain maximum chemical sensitivity and selectivity, the sensing structure must be fabricated whereby the current conduction is electric field dominated, and is characterized by the voltage-current relationship in an ohmic region followed by an SCLC region. FIG. 12 clearly shows this relationship. To take advantage of the voltage-current response of such a structure, the sensing device should preferably operate in the SCLC region when exposed to the target chemical, and approach the ohmic region when there is no target chemical present. The combination of an ohmic region with an SCLC region can be achieved when layered structures such as those described herein are comprised of a wide band-gap semiconductor such as diamond and silicon carbide.

It is well known in the art that the device current I, when a solid state device is operating in the ohmic region, is determined as follows:

$$I = qp_o u_p E = qp_o u_p V/L$$

When the device is fabricated to operate in the SCLC region, i.e., when sensor current is primarily space-charge limited, the device current I is determined as:

$$I = \epsilon u_p E^n/L = \epsilon u_p V^n/L^m \text{ (where } n=2 \text{ or greater and } m=3\text{)}$$

where $p_o$ is the thermal equilibrium carrier concentration, $u_p$ is the carrier mobility, $\epsilon$ is the dielectric constant of the intrinsic diamond, E is the electric field across the insulating-diamond layer of the device, V is the applied voltage across the intrinsic diamond layer, and L is the thickness of the intrinsic diamond.

Figure 1:
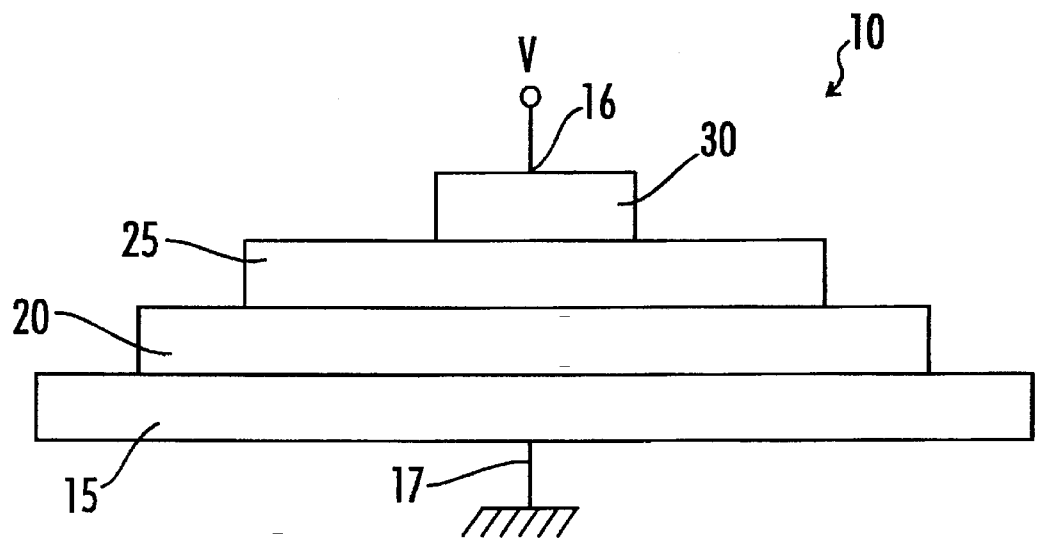
FIG. 1 is a cut-away side-view of a first embodiment of the chemical sensing device having a chemically sensitive electrode, an intrinsic diamond layer, and a doped diamond layer deposited on a conducting substrate.

FIG. 1 shows a first embodiment of a solid state chemical sensor 10 of the present invention. A sensing structure is fabricated in which a doped diamond layer 20 is deposited on a conductive substrate 15, and an intrinsic (undoped) diamond layer 25 is deposited on the doped diamond layer 20. A chemically sensitive electrode 30, a catalytic metal for example, is then deposited on top of the intrinsic diamond layer 25. The thickness and trapping defect density of the intrinsic diamond layer 25, and the doping concentration of the doped diamond layer 20, are selected and fabricated to form a sensing structure which will operate in the SCLC region when the device is exposed to a target chemical.

To provide for the application of a bias voltage as well as measurement points, a first ohmic contact 16 is formed on the electrode 30 and a second ohmic contact 17 is formed on the conductive substrate 15.

Taking the case of a sensing device optimized for detection of hydrogen gas, absorption of hydrogen dipoles at the gas-sensitive electrode/intrinsic diamond interface causes a voltage drop across the hydrogen dipoles and leads to a decrease in applied electric field across the intrinsic diamond layer 25. This leads to a corresponding decrease in current through the sensing structure. The change in sensor current, which is indicative of the presence of hydrogen, can be ascertained through suitable test equipment well know in the art (not shown) electrically connected to first and second contacts 16 and 17. If a "smart" interface, also of conventional design, receives dam from the test equipment, even the amount of hydrogen gas present can be determined.

In order to construct a high performance solid state sensing structure for chemical sensing, several structural parameters are needed to fabricate a highly sensitive and selective diamond-based chemical/gas sensor. In order to have space charge limited current of significant magnitude and use it for chemical sensing, at least one of either the chemical-sensitive-electrode 30 or doped diamond layer 20 must make ohmic contact to the intrinsic diamond layer 25. The concept of an ohmic contact to an insulator (intrinsic diamond) is perhaps not a common one and needs to be defined. An ohmic contact is used here to mean an electrode that supplies an excess or a reservoir of carders ready to enter the insulator (intrinsic diamond) as needed.

Also, the intrinsic diamond layer 25 should be fabricated to have a trapping defect density that is less than a critical value. If the trapping defect density exceeds that value, the SCLC is reduced to a value whereby the chemical sensor is not effective. In intrinsic diamond, the maximum trapping defect density is typically in the range of $10^{18}/cm^2$. The presence of excessive traps in the intrinsic diamond layer 25 lowers the drift mobility of carders and thereby the magnitude of the space-charge-limited currents. Trapping defect densities of greater than $10^{18}/cm^2$ would be sufficient to reduce the space-charge-limited currents to almost an unmeasurable and hence useless value.

The thickness of the intrinsic diamond layer 25 is also important. The operating principle of this chemical/gas sensor is based on the change in electric field across the intrinsic diamond layer 25 attributed to different mechanisms. These mechanisms include: a) change in effective work function of the catalytic metal in electrode 30 upon chemical exposure; b) a change in dipole layer which is attributed to the change in chemical species at the catalyst/chemical-sensitive-oxide interface of the sensing structure, when the chemically sensitive electrode 30 includes a metal oxide layer 31 combined with a catalyst 32 (FIG. 4); c) a change in the interface state density at the interface region due to chemical species; or d) change in charge density in the chemical-sensitive electrode 30 and consequently the field distribution across the intrinsic diamond layer 25. The intrinsic diamond layer 25 must be thin enough so that a chemical-induced electric field change can be coupled through the intrinsic diamond layer 25 and hence achieve the SCLC characteristics.

The thickness of the intrinsic diamond layer 25 is also an important fabrication parameter when optimizing the device 10 and to achieve the appropriate SCLC to produce a sensor with the dynamic sensitivity range required for a specific gas/chemical detection or application. In diamond, the preferred thickness will typically fall in the range 0.01 –0.5 μm.

In order to reduce the series resistance effect and to provide good back (second) ohmic contact 17, a doping concentration of $10^{18}$–$8 \times 10^{19}$ cm$^{-3}$ of boron is used in doped diamond layer 20 to form a suitable semiconductor. The doped diamond layer 20 is aim used as an electrode to provide a hole reservoir or a means for injecting holes into the intrinsic diamond layer 25 under bias.

Preferably, annealed intrinsic diamond post deposition films are required to achieve high electrical resistivity (over $10^{12}$ ohm-cm) and a trapping defect density of less than $10^{18}/cm^3$ to support the SCLC conduction domination as described.

Plasma-enhanced-chemical-vapor-deposition (PECVD) diamond film is selectively grown on the surface of the supporting substrate 15 by microwave plasma chemical vapor deposition (MPCVD), typically using a mixture of hydrogen and methane gas, and a substrate temperature of 850° C. The growth rate under these conditions is nominally 0.5 μm per hour. The diamond films are annealed for one minute at 850° C. in argon. Typical Raman spectroscopy of diamond films fabricated shows a 1332 cm$^{-1}$ peak indicating characteristic sp$^3$ bonding and a very slight graphite peak at 1580 cm$^{-1}$, indicating a good diamond film. Doped diamond layer 20 is prepared by depositing p-type polycrystalline diamond film of varying thickness, typically 1–5 μm thick, on the surface of supporting substrate 15. The diamond film is then doped with boron (typically a boron concentration of $10^{18}$–$8 \times 10^{19}$ cm$^{-3}$) using an in situ boron compound solid source doping method. This reduces the series resistance effect and provides good back ohmic contact. An intrinsic diamond interfacial layer 25 of varying thickness, preferably 0.01 –0.5 μm, is then deposited on the doped diamond layer 20. Typically, post rapid thermal annealed intrinsic diamond films have shown high electrical resistivity, over $10^{12}$ ohm-cm, which indicate an approximately intrinsic condition. As noted above, the thickness of the intrinsic diamond layer 20 can be varied to achieve the appropriate SCLC to produce a sensor with the dynamic sensitivity range as required for a specific gas/chemical detection or application. The substrate is preferably formed of tungsten, molybdenum, or other conductive layer which also supplies mechanical support.

Finally, one of various types of a chemical-sensitive electrode 30 is deposited onto the upper surface of intrinsic diamond layer 25.

Figure 2:
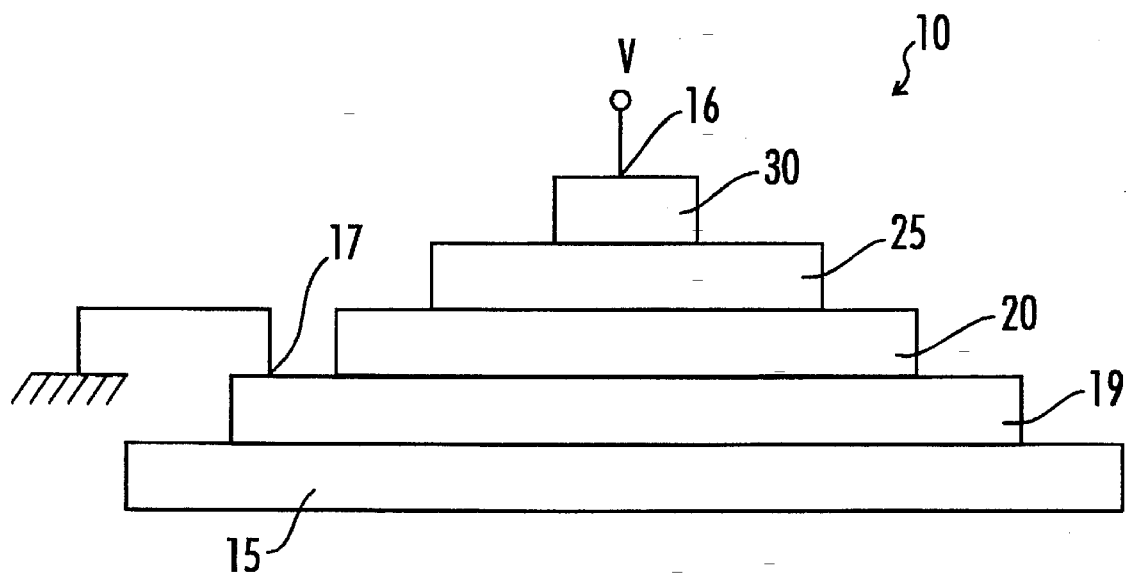
FIG. 2 is a cut-away side view of a second embodiment of the chemical sensing device having a chemically sensitive electrode, an intrinsic diamond layer, a doped diamond layer, and a conductive film-deposited on an insulating substrate.

FIG. 2 illustrates a second embodiment of the device 10 in which substrate 15 is formed of a material such as glass, alumina, or silicon. The silicon substrate may be anisotropically or otherwise etched from the backside (KOH/methanol solution, etch differential of 400:1, (100):(111)) to remove a portion of the silicon to enhance mass heat loss. A conductive film 19 is applied between the substrate 15 and doped diamond layer 20 so that the second ohmic contact 17 can be fabricated on the lower surface of doped diamond layer 20. The conductive film 19 can be applied directly on substrate 15 by vacuum evaporating gold or other suitable metal. Or, the metal film can be applied through an aperture (not shown) through substrate 15.

Figure 3:
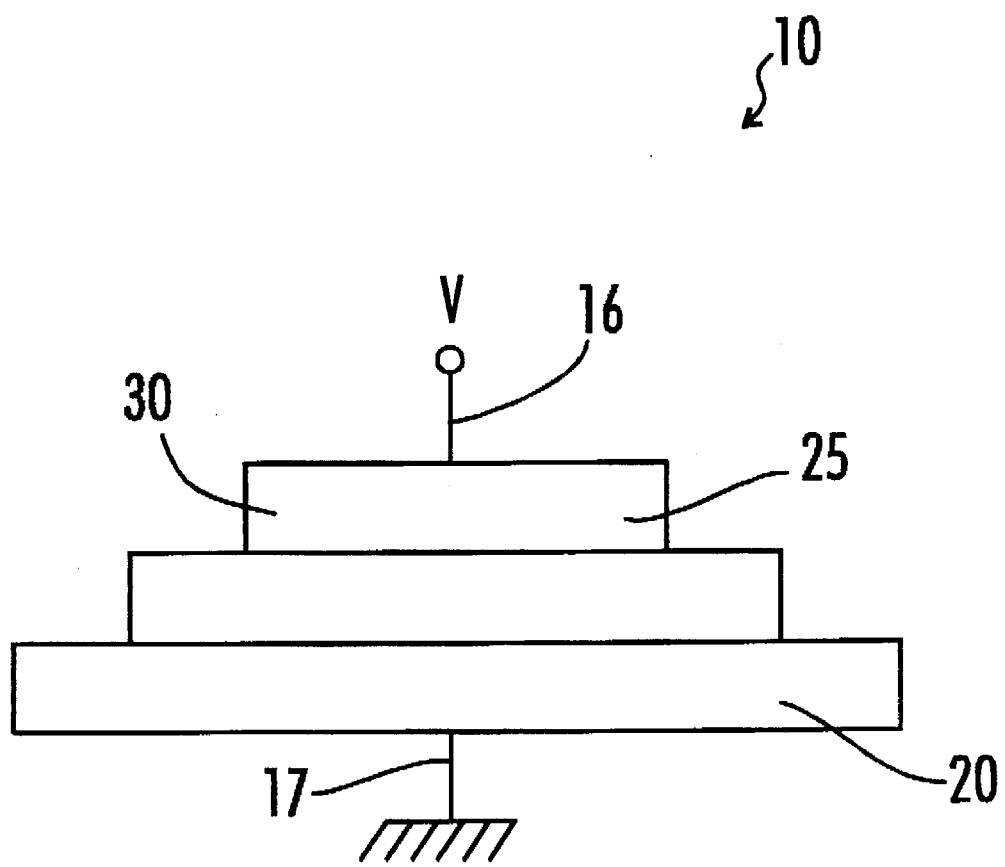
FIG. 3 is a cut-away side view of a third embodiment of the chemical sensing device having a chemically sensitive electrode, an intrinsic diamond layer, and a doped diamond layer, with a conductive film on the bottom device to form an ohmic contact.

In FIG. 3, a third embodiment of device 10 having a sensing structure, comprising a chemically sensitive electrode 30, an intrinsic diamond layer 25, and doped diamond layer 20, with the doped diamond layer 20 also functioning as a supporting substrate. Accordingly, a metal film is deposited on the lower surface of doped diamond layer 20 to create a second ohmic contact 17.

As described, the chemical-sensitive-electrode/intrinsic diamond/p-diamond/substrate layered structure is elegantly simple, economically manufacturable and inherently rugged. Its principle of operation is similar for all the sensors, but its enhanced performance in sensitivity and selectivity arises also from the choice of the chemical sensitive layers. The use of CVD diamond as a common material base is another fundamental and inherent innovative feature. Furthermore, silicon microfabrication techniques can be employed, where low cost, batch fabricated devices can be created first, followed by selective deposition of gas/chemical-sensitive materials tailored toward a specific gas/chemical detection. The diamond sensor output can be readily integrated into control circuitry for any form of signal conditioning desired.

Similar sensor performance can be achieved using different sensing structure variations, as optimized for selectivity in sensing certain chemicals. These different sensor structures are illustrated as follows:

FIG. 1: electrode/insulator/semiconductor/conducting substrate structures;

FIG. 2: electrode/insulator/semiconductor/conductor/non-conducting substrate structures;

FIG. 3: electrode/insulator/semiconductor structures

Figure 4:
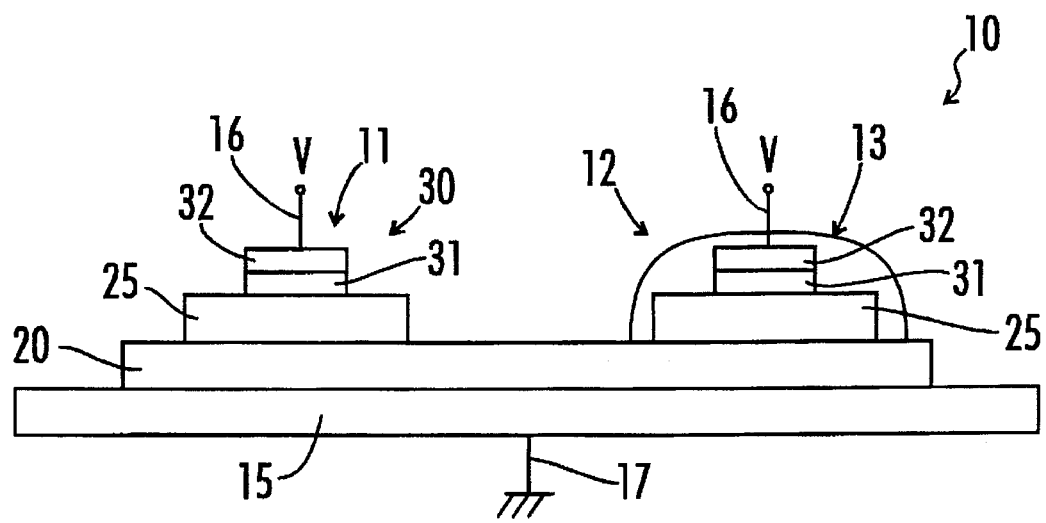
FIG. 4 is a cut-away side view of a fourth embodiment of the chemical sensing device having a chemically sensitive electrode structure, an intrinsic diamond layer, and a doped diamond layer forming a chemical sensitive structure on a conductive substrate, and further showing an identically layered second chemically sensitive structure covered by a passivation layer to isolate the second sensing structure from ambient chemicals.
Figure 5:
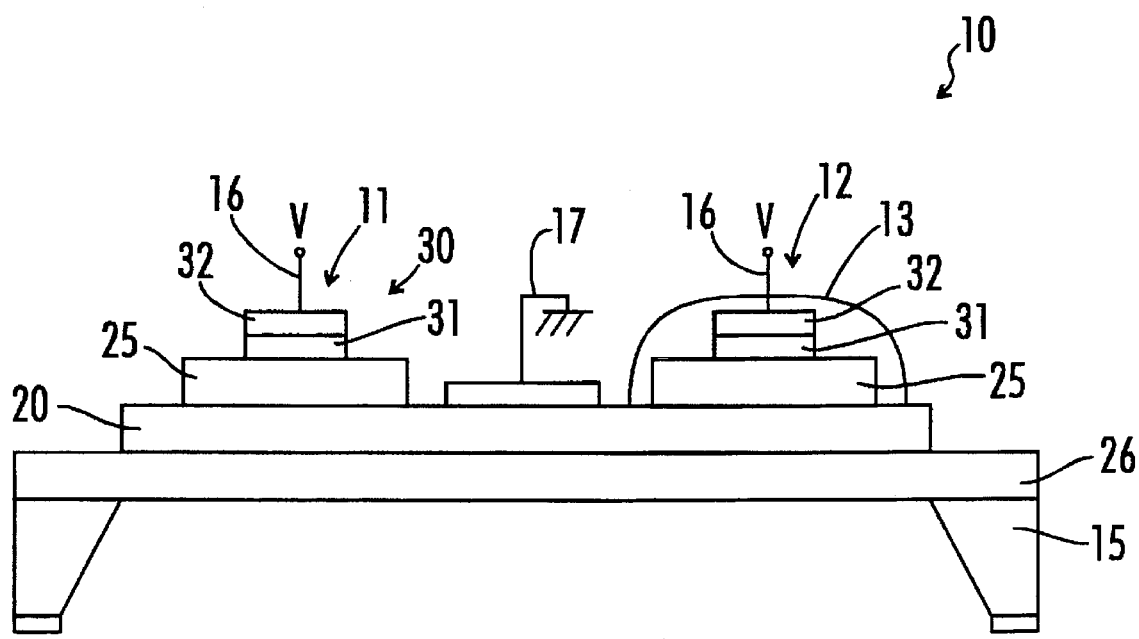
FIG. 5 is a cut-away side view of a fifth embodiment of the chemical sensing device in which a chemically sensitive electrode, a first intrinsic diamond layer, a doped diamond layer, and a second intrinsic diamond layer are deposited on a substrate.
Figure 6:
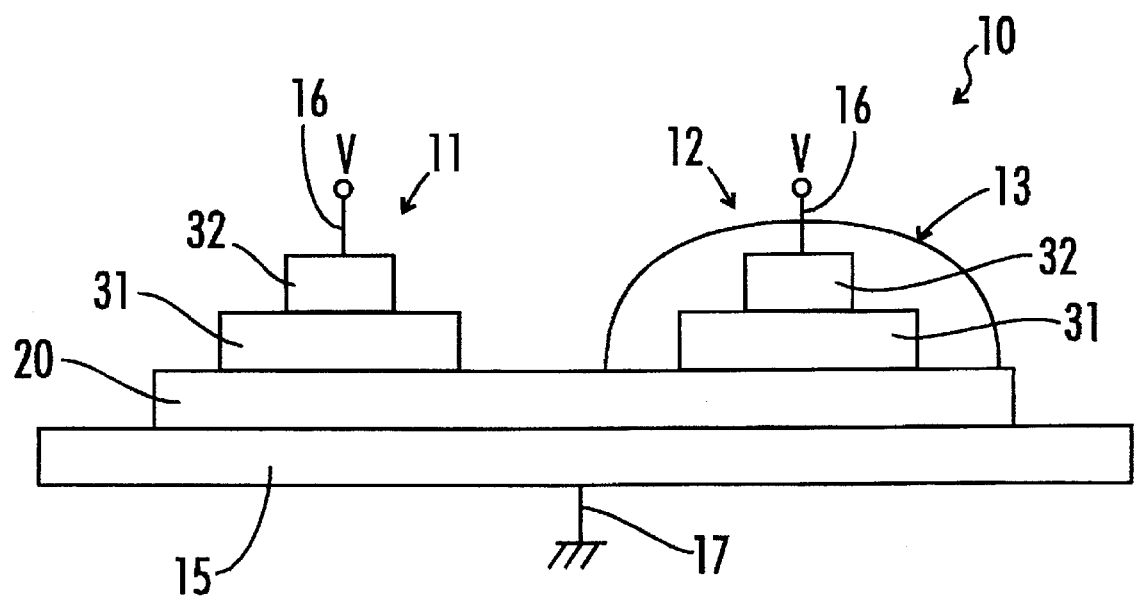
FIG. 6 is a cut-away side view of a sixth embodiment of the chemical sensing device having a chemically sensitive electrode and a doped diamond layer deposited on a conductive substrate and further showing an isolated sensing structure on the same substrate.
Figure 7:
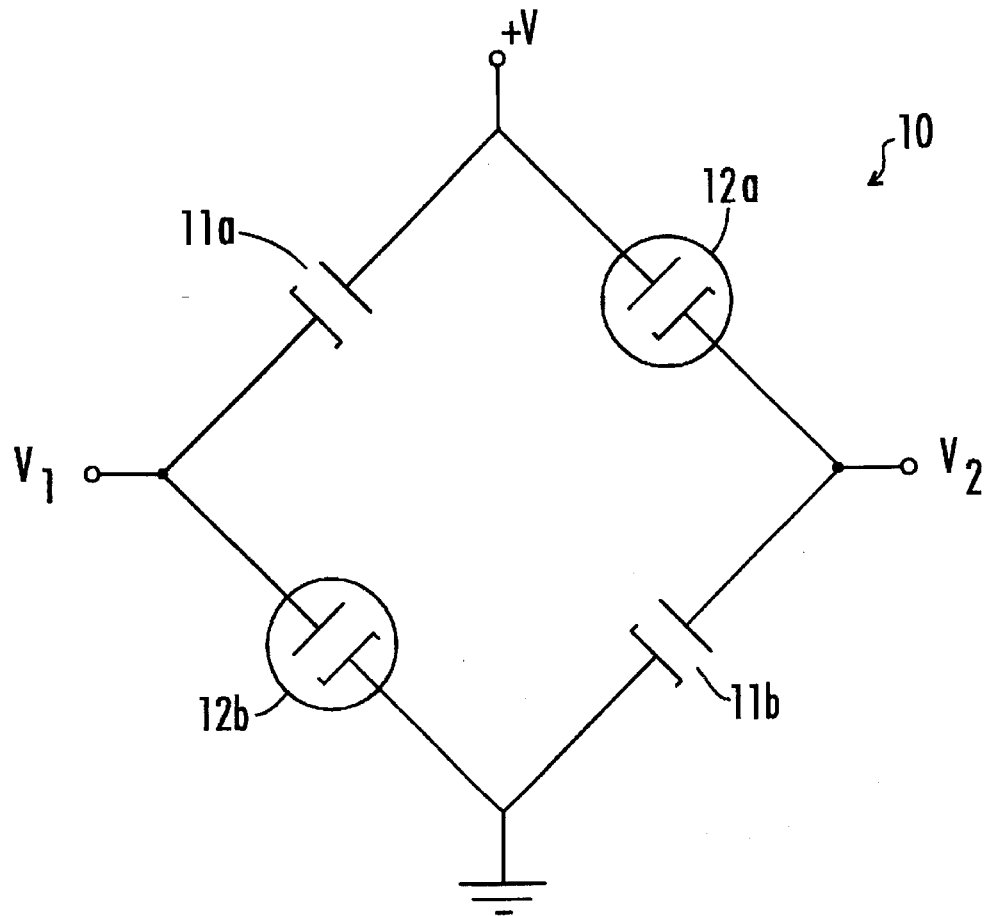
FIG. 7 is a schematic drawing of a seventh embodiment of the chemical sensor device in which two chemical sensing structures are arranged on a substrate in a bridge configuration, with two isolated sensing structures to provide a temperature compensating chemical sensor array.
Figure 8:
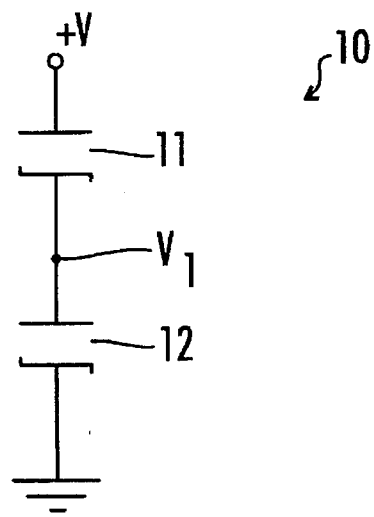
FIG. 8 is a schematic diagram of an eighth embodiment of the chemical sensing device in which a chemical sensing structure and an identically fabricated isolated sensing structure are arranged in series on a common substrate, to provide temperature compensation for the sensing device.

FIG. 4: electrode/insulator/semiconductor/conducting substrate structures, with isolated sensing structure for temperature compensation;

FIG. 5: electrode/insulator/semiconductor/insulator/non-conducting substrate structures (with or without temperature compensation);

FIG. 6: electrode/semiconductor/conducting substrate structures (with or without temperature compensation);

FIGS. 7 and 8: devices with bridged or series arranged sensor arrays for temperature compensation.

As described, the semiconductor is polycrystalline or monocrystalline diamond of doping concentration typically of $10^{18}$ to $8 \times 10^{19}$ cm$^{-3}$. The insulator is an undoped (intrinsic) poly or mono diamond, $SiO_2$, $Si_3N_4$, or their combinations.

The chemical sensitive electrode can be a catalytic metal, a metal oxide, a solid electrolyte, an organic material, a metal oxide coated with a thin layer of catalyst, a solid electrolyte coated with a thin layer of catalyst, and an organic material coated with a thin layer of catalyst.

Suitable metal-oxides include $SnO_x$, ZnO, CuO, $TiO_2$ or any other gas/chemical-sensitive metal-oxide. The metal-oxide can be undoped, doped with additives, or, as noted, coated with a thin layer of catalyst. A preferred solid-electrolyte includes halide ion conductor (such as $LaF_3$), or zirconia. Suitable catalysts include Pd, Pt, or any other catalytic active metal. The organic material can be Langmuir-Blodgett film.

The catalyst layer should be very thin, typically less than 50 angstroms. The catalyst provides an alternative reaction path with less reaction activation energy for sensing to occur. For example in a Pt/SnO$_x$/intrinsic diamond/p-diamond structure, Pt is used as a catalyst layer. The catalyst layer dissociates certain gas (e.g. oxygen) molecules into atomic gas (e.g. oxygen) atoms or converts a hydrocarbon into an activated hydrocarbon complex, thereby enhancing a specific chemical detection and selectivity.

The chemisorptive and catalytic activities of metal-oxides, organic materials or solid electrolytes can be enhanced significantly by incorporating small amounts of catalytically active metals. In order to promote chemical sensitivity, an additive should effectively influence the semiconductive or ionic properties of the chemical sensing material. Two types of interaction between the additives and chemical-sensitive material have been proposed [29,30], chemical and electronic. In the former, additives assist the redox processes of semiconductive oxides. At appropriate temperatures, the adsorbed molecules are activated (dissociated, or elevated to an excited state) by the catalytic metal component. These molecules then diffuse onto the oxide where they undergo rapid chemical interaction with other adsorbates or with the oxide, thereby enhancing chemisorptive and catalytic actions. In electronic activation, additives interact electronically with the semiconductor as electron donors or acceptors.

It is well known that the most active catalytic metals are the noble metals such as Pt, Pd, Rh, and Ir. These metals, with their partially filled bands, are particularly active for reactions, with the d-orbital electrons involved in the chemisorption process. The heat of gas adsorption on the noble metals is sufficiently low to allow a relatively low activation energy and consequently a rapid rate of reaction. The catalytic activities of these materials can be employed in chemical sensors. Therefore, by proper combinations of catalytically active metals, metal-oxide or solid electrolyte with the unique properties of diamond, high performance chemical/gas sensor of wide dynamic range can be achieved.

A preferred chemical sensing electrode 30 for sensing hydrogen or hydrogen gases would be made of a catalytic metal or metal alloy. For use of device 10 as an oxygen sensor, electrode 30 would be manufactured from a solid electrolyte, such as LaF$_3$, with a coating of platinum or other catalytic metal. Alternatively, a metal-oxide (SnO$_x$, ZnO, CuO, TiO$_2$) with a catalytic metal coating would be suitable.

A carbon monoxide sensor would have an electrode 30 using SnO$_x$ or ZnO in combination with platinum or palladium. A nitrogen oxides gas (NO$_x$) could be sensed with a device 10 having an electrode made of SnO$_x$. An electrode 30 using SnO$_2$/CuO bilayers would be sensitive to H$_2$S gas.

The device 10 would also be of benefit in determining the presence of a reducing gas by using oxygen as the target chemical under ambient conditions. Accordingly, the presence of a reducing gas would reduce the concentration of the chemisorbed oxygen at the electrode, causing a shift in the voltage—current relationship curve in device 10 from the SCLC region towards the ohmic region. This shift could then be measured by conventional means and used to calculate the concentration of reducing gas.

The high performance chemical sensing device can be fabricated with a first sensing structure 11 is fabricated integrally with a second sensing structure 12 on a single conductive substrate 15, as seen for example on FIG. 4. The second sensing structure 12 is used for temperature compensation. Both the first and second sensing structures 11 and 12 can be fabricated under the same identical process run. However, the second sensing structure 12 is also covered with a passivation layer 13 to isolate structure 12 from external chemicals. Therefore, second sensing structure 12 provides an output response resulting only from temperature changes. By comparing the response of the first sensing structure 11 with that of second sensing structure 12, the influence of temperature is removed and the effect of chemical concentration determined independent of temperature.

The embodiment of device 10 shown in FIG. 5 is fabricated in a manner similar to the embodiment of FIG. 4, except that first and second sensing structures 11 and 12 are mounted on an insulating substrate 15. A diaphragm 26, preferably comprising a second layer of intrinsic diamond, is deposited between substrate 15 and doped diamond layer 20. In this embodiment, diaphragm 26 assists in thermal management, electrical isolation, and structural support for device 10. The second ohmic contact 17 to device 10 is attached to the upper surface of doped diamond layer 20. Also in this embodiment, as in FIG. 4 and FIG. 6, chemical sensitive electrode 30 is actually fabricated in layers, with a lower layer 31 of metal oxide, solid electrolyte, or organic material, coated with an upper layer 32 of catalyst.

FIG. 6 is another embodiment of device 10 similar to that of FIG. 4, but without an intrinsic diamond layer. Such an embodiment would be useful when using a wide band-gap chemical-sensitive semiconductor or insulator in electrode 30 to achieve SCLC conditions at the electrode/doped diamond interface without the use of intrinsic diamond.

FIG. 7 shows another preferred embodiment of a chemical sensing device 10 having a bridged array of four sensing structures, 11a, 11b, 12a, and 12b. Structures 12a and 12b encapsulated in a passivation layer 13 (FIG. 4) to isolate them from the gas environment. Ambient temperature changes effect all four structures equally, and therefore, the difference in voltage measured at terminals V$_2$ and V$_1$, does not change. However, changes in ambient gas concentration effect structures 11a and 11b while not so effecting structures 12a and 12b. Therefore, the voltage difference, V$_2$-V$_1$, responds only to changes in gas concentration and is relatively unaffected in changes in ambient temperature. This integrated device 10 can be fabricated on the same substrate because all four sensing structures contain identical deposited layers, excluding the passivation layer, making an integrated, cost effective, manufacturable sensing device which will operate over a wide range of temperatures including high temperatures.

A half-bridge sensing device 10, having a first sensing structure 11 in series with a second, encapsulated sensing structure 12, is shown in FIG. 8. In this configuration, device 10 will provide a response to ambient gas or liquid ion concentration sensitivity with yearly reduced sensitivity to ambient temperature, but with less overall sensitivity than the full bridge structure of FIG. 7.

Figure 9:
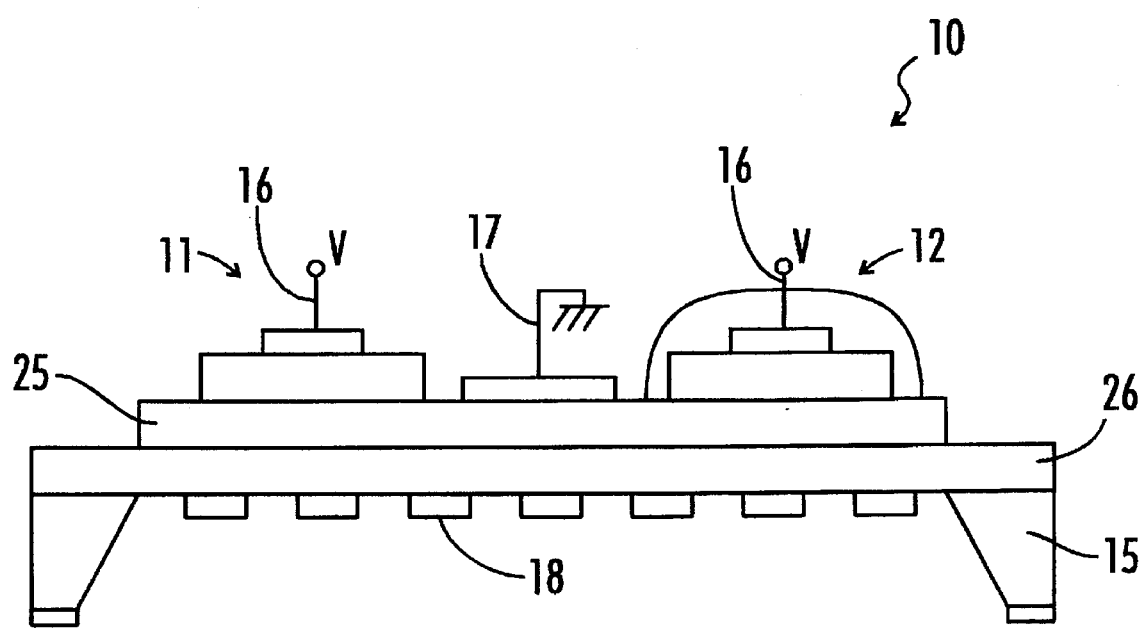
FIG. 9 is a cut-away side view of a ninth embodiment of the chemical sensing device having a sensing structure arrangement substantially as shown in FIG. 5 and further including a device heater integrally formed with the device.

A diamond-based chemical/gas sensing device 10 with an integral temperature sensor (second sensing structure 12) and a device heater incorporated into the same sensor chip is shown in FIG. 9. This novel approach utilizes the inert properties of diamond as an automatic etch-stop layer thereby providing a means to precisely construct a non-diamond heating element 18 attached to or suspended underneath a diaphragm 26. The suspended heating element 18 would reduce electrical interference. The built-in heater can be constructed underneath but electrically insulated from first sensing structure 11 and second sensing structure 12. The diaphragm 26 (preferably fabricated of intrinsic diamond layer) is used for electrical insulation, heat dissipation, and support of the sensing structures. The heating element 18 can be fabricated by deep boron diffusion on silicon prior to the diamond deposition. This approach also obviates the need for an aperture and ion implantation of diamond, thereby simplifying the fabrication process significantly, increasing yield and reducing cost.

The heater can be employed in a temperature scanning technique whereby the sensing device is heated to different temperatures, with sensor responses measured at each temperature. For example, the use of diamond in device 10 allows rapid temperature scanning across a range from room temperature to 600 degrees C. Depending on the particular chemicals being targeted, this range can be adjusted, along with the scanning rate and sampling ram. Consequently, the effects of chemical interference on the presently invented family of diamond-based sensors can be minimized. The temperature scanning technique provides a good means of enhancing sensitivity, selectivity and reducing interference effects. This method can be applied very robustly in the present invention because of the inherent wide temperature capability and good thermal conductivity of diamond. By tracking the I-V shift of the device as the temperature scans through the characteristic adsorption-temperature peaks, the type and amount of chemicals present can be determined. Therefore, the use of a temperature scanning technique would provide a means to reduce and minimize gas interference.

The heating element 18 can also be used to substantially elevate the operating temperature of device 10 to a point where water vapor which may otherwise be present is heat dissipated, eliminating such vapor as a complicating factor in chemical detection.

Generally, the presence and concentration of a target chemical proximate the device 10 be determined by measuring a change in current through the device. However, in some applications, similar data can be obtained by measuring a change in device capacitance using conventional capacitance measuring techniques and equipment.

A pragmatic, cost-effective approach which is amenable to high volume manufacturing can be utilized in the microelectronic chemical/gas sensor described. The novel employment of planar microfabrication and PECVD diamond technologies can be utilized to fabricate a genetic diamond-based structure and integration of various chemical-sensitive structures tailored to specific applications.

The chemical sensing device of this invention senses chemical species at chemical-sensitive electrodes only and has no need for an "aperture" or other structural additions or complexities that affect cost or performance adversely.

Further, the fabrication steps to achieve device structure employ standard microelectronic integrated circuit technology such as photolithography, etching and depositions by batch-mode which allow production of hundreds of devices on a common substrate at high yield and reproducibility. Further, this uniform batch processing allows multiple sensing structure formation per chip, where the sensors can be selectively coated and connected in bridge and similar configurations that achieve advances in control, sensitivity and precision, otherwise impossible. Further, the microelectronic processing allows the diamond sensors to be made very small with high packing density.

Thus, although there have been described particular embodiments of the present invention of a new and useful "Chemical Sensor Utilizing a Chemically Sensitive Electrode in Combination with Thin Diamond Layers," it is not intended that such references be construed as limitations upon the scope of this invention except as set forth in the following claims. Further, although there have been described certain dimensions and specifications used in the preferred embodiment, it is not intended that such be construed as limitations upon the scope of this invention except as set forth in the following claims.

What is claimed is:

1. A device for sensing the proximity of a target chemical, the device comprising:
   a. a first chemical sensing structure defined by a plurality of discrete device layers, including at least first and second device layers, the device layers generally arranged from a top of the device to a bottom of the device, each layer mechanically and electrically bonded to each adjacent layer;
   b. the first layer comprising a chemical sensitive electrode including a first electrical contact means for applying a voltage to the device;
   c. the second layer comprising a doped diamond layer;
   d. a second electrical contact means for applying a voltage to the device, the second electrical contact means electrically connected to one of the device layers; and
   e. the sensing structure forming a solid state rectifier when exposed to the target chemical, the rectifier characterized by a voltage-current relationship dominated by space charge limited current.

2. The device of claim 1 wherein the chemical sensitive electrode comprises one or more materials selected from the group of material combinations consisting of: a catalytic metal; a metal oxide; a solid electrolyte; an organic material; a catalyst with a metal oxide; a catalyst with a solid electrolyte; and a catalyst with an organic material.

3. The device of claim 2, the first chemical sensing structure further comprising a third device layer adjacent to the doped diamond layer, the third device layer comprising a first intrinsic diamond layer.

4. The device of claim 3 wherein the second electrical contact means comprises a conductive film mechanically and electrically contacting the doped diamond layer.

5. The device of claim 3 wherein the second electrical contact means comprises a conductive substrate supporting the device.

6. The device of claim 3, further comprising integral heater means for heating the device.

7. The device of claim 5 further comprising a solid state temperature sensing means for sensing the temperature proximate the device.

8. The device of claim 7, the temperature sensing means comprising a second chemical sensing structure formed on the substrate adjacent the first chemical sensing structure, the second chemical sensing structure having discrete device layers identical to the device layers of the first chemical sensing structure, the temperature sensing means including passivation layer means to isolate the second chemical sensing structure from the target chemical.

9. The device of claim 8, further comprising integral heater means for heating the device.

10. The device of claim 3 wherein the second electrical contact means is formed as an ohmic contact to the doped diamond layer, the device further comprising a substrate supporting the device and a second intrinsic diamond layer between the substrate and the doped diamond layer.

11. The device of claim 10 further comprising a solid state temperature sensing means for sensing the temperature proximate the device.

12. The device of claim 11, the temperature sensing means comprising a second chemical sensing structure formed on the substrate adjacent the first chemical sensing structure, the second chemical sensing structure having discrete device layers identical to the device layers of the first chemical sensing structure, the temperature sensing means including passivation layer means to isolate the second chemical sensing structure from the target chemical.

13. A device for sensing the presence of a chemical, the device comprising:
   a. a chemical sensitive electrode having an upper electrode surface and a lower electrode surface;
   b. an intrinsic diamond layer having a lower intrinsic diamond surface and an upper intrinsic diamond surface which joins the lower electrode surface;
   c. a semiconducting diamond layer having a lower p-diamond surface and an upper p-diamond surface joined to the lower intrinsic diamond surface;
   d. a substrate having an upper substrate surface joined to the lower p-diamond surface;and
   e. the chemical sensitive electrode, intrinsic diamond layer, and the semiconducting diamond layer defining a chemical sensing structure which, in the presence of the chemical, forms a rectifying structure in which conduction of current through the device is predominantly space charge limited current.

14. The device of claim 13 wherein at least one of the lower electrode surface and the upper p-diamond surface form an ohmic contact with the intrinsic diamond layer.

15. The device of claim 14 wherein the chemical sensing structure, in the absence of the chemical, forms a non-rectifying structure.

16. The device of claim 15 wherein the substrate comprises a conductive material to define a back ohmic contact on the device.

17. The device of claim 15 wherein the substrate comprises a non-conductive material, the device further comprising an ohmic contact on the upper p-diamond surface.

18. A solid state chemical sensor comprising a substrate, a first electrical contact to a doped polycrystalline diamond region deposited on an upper surface of the substrate, an insulating polycrystalline diamond region deposited on an upper surface of the doped polycrystalline diamond region, a chemically sensitive electrode electrically contacting an upper surface of the insulating polycrystalline diamond region, a second electrical contact to the device attached to the chemically sensitive electrode, and the sensor not having a second doped diamond region which has a higher doping concentration level than the doped polycrystalline diamond region.

19. The chemical sensor of claim 18 wherein the doped polycrystalline diamond region comprises p-diamond having a doping concentration of between $1\times10^{18}$ and $8\times10^{19}/cm^3$.

20. The chemical sensor of claim 19 wherein the insulating polycrystalline diamond region has a trapping defect density of less than $10^{18}/cm^2$.

21. The chemical sensor of claim 20 wherein the insulating polycrystalline diamond region comprises annealed intrinsic PECVD diamond deposited at a thickness of between 0.01 and 0.5 microns.

22. The chemical sensor of claim 18 wherein the doped polycrystalline diamond region, on comprises n-diamond.

23. A device for detecting the presence of a target chemical, the device comprising a substrate, a region of doped diamond deposited on the substrate, a region of intrinsic diamond deposited on the doped diamond region, and a chemical sensing electrode formed on the intrinsic diamond region, the device functioning as a solid state rectifier dominated by space charge limited current when the device is exposed to the target chemical.

24. The device of claim 23 wherein the target chemical is oxygen and the chemical sensing electrode comprises platinum joined with a material selected from the group consisting of $LaF_3$, $SnO_x$, ZnO, and $TiO_2$.

25. The device of claim 23 wherein the target chemical is hydrogen gas and the chemical sensing electrode comprises a catalytic metal.

26. The device of claim 23 wherein the target chemical is carbon monoxide and the chemical sensing electrode comprises a material combination selected from the group consisting of palladium with $SnO_x$, platinum with $SnO_x$, and platinum with ZnO.

27. The device of claim 23 wherein the target chemical is $NO_x$ and the chemical sensing electrode comprises a $SnO_x$.

28. The device of claim 23 wherein the target chemical is hydrogen sulfide and the chemical sensing electrode comprises a material combination selected from the group consisting of palladium with $SnO_2$/CuO bilayers.

29. A solid state chemical sensor comprising a substrate, a first electrical contact to a doped polycrystalline diamond region deposited on an upper surface of the substrate, an insulating polycrystalline diamond region deposited on an upper surface of the doped polycrystalline diamond region, a chemically sensitive electrode electrically contacting an upper surface of the insulating polycrystalline diamond region, and a second electrical contact to the device attached to the chemically sensitive electrode, wherein the doped polycrystalline diamond region comprises p-diamond having a doping concentration of greater than $1\times10^{18}/cm^3$.

30. A device for sensing the proximity of a target chemical, the device comprising:
   a. a first chemical sensing structure defined by a plurality of discrete device layers, including at least first, second, and third device layers, the device layers generally arranged from a top of the device to a bottom of the device, each layer mechanically and electrically bonded to each adjacent layer;
   b. the first device layer comprising a chemical sensitive electrode including a first electrical contact means for applying a voltage to the device;
   c. the second device layer comprising an intrinsic diamond layer;
   d. the third device layer comprising a doped diamond layer;
   e. a second electrical contact means for applying a voltage to the device, the second electrical contact means electrically connected to the third device layer; and
   f. the sensing structure characterized by a voltage-current relationship in which current conduction through the device includes a transition between a space charged limited current mode to an ohmic conduction mode as a function of bias applied to the sensing structure.

31. A gas sensor comprising a solid state rectifying structure formed of a plurality of semiconductor layers, the rectifier structure having a voltage-current relationship in which the current through the rectifying structure, at a constant applied voltage, decreases when the sensor is exposed to a reducing gas.

32. A gas sensor comprising a solid state rectifying structure formed of a plurality of semiconductor layers, the rectifier structure having a voltage-current relationship in which the voltage across through the rectifying structure, at a constant current through the sensor, increases when the sensor is exposed to a reducing gas.

33. A device for sensing the presence of a target chemical, the device comprising:

a. a first chemical sensing structure defined by a plurality of discrete device layers, including at least first, second, and third device layers, the device layers generally arranged from a top of the device to a bottom of the device, each layer mechanically and electrically bonded to each adjacent layer;

b. the first device layer comprising a chemical sensitive electrode including a first electrical contact means for applying a voltage to the device;

c. the second device layer comprising an intrinsic diamond layer;

d. the third device layer comprising a doped diamond layer;

e. a second electrical contact means for applying a voltage to the device, the second electrical contact means electrically connected to one of the device layers; and f. the sensing structure characterized by a voltage-current relationship in which the device can operate in a space charged limited current mode and in an ohmic conduction mode as a function of bias applied to the sensing structure.

34. A device for sensing the proximity of a target chemical, the device comprising:

a. a first chemical sensing structure defined by a plurality of discrete device layers, including at least first, second, and third device layers, the device layers generally arranged from a top of the device to a bottom of the device, each layer mechanically and electrically bonded to each adjacent layer;

b. the first device layer comprising a chemical sensitive electrode including a first electrical contact means for applying a voltage to the device;

c. the second device layer comprising an intrinsic diamond layer;

d. the third device layer comprising a doped diamond layer;

e. a second electrical contact means for applying a voltage to the device, the second electrical contact means electrically connected to the third device layer; and f. the sensing structure characterized by a voltage-current relationship in which the device does not conduct current principally by thermionic field emission.

35. A solid state chemical sensor consisting of a substrate, a first electrical contact to a doped polycrystalline diamond region deposited on an upper surface of the substrate, an insulating polycrystalline diamond region deposited on an upper surface of the doped polycrystalline diamond region, a chemically sensitive electrode eclectically contacting an upper surface of the insulating polycrystalline diamond region, and a second electrical contact to the device attached to the chemically sensitive electrode.

* * * * *